US011479580B2

(12) United States Patent
Jonca et al.

(10) Patent No.: US 11,479,580 B2
(45) Date of Patent: *Oct. 25, 2022

(54) POLYPEPTIDE EXPRESSED IN THE STRATUM CORNEUM AND USE THEREOF

(71) Applicants: CENTRE NATIONAL DE LA RECHERCHE SCIENTIFIQUE—CNRS, Paris (FR); UNIVERSITE PAUL SABATIER TOULOUSE III, Toulouse (FR)

(72) Inventors: Nathalie Jonca, Lagardelle sur Leze (FR); Eve Toulza, Nyls Ponteilla (FR); Gaelle Saintigny, Paris (FR); Guy Serre, Toulouse (FR); Marina Weber Vivat, Saint Paulet (FR)

(73) Assignees: CENTRE NATIONAL DE LA RECHERCHE SCIENTIFIQUE—CNRS, Paris (FR); UNIVERSITE PAUL SABATIER TOULOUSE III, Toulouse (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/138,124

(22) Filed: Sep. 21, 2018

(65) Prior Publication Data

US 2019/0010191 A1 Jan. 10, 2019

Related U.S. Application Data

(60) Continuation of application No. 15/447,968, filed on Mar. 2, 2017, now abandoned, which is a continuation-in-part of application No. 14/736,666, filed on Jun. 11, 2015, now Pat. No. 9,617,307, which is a division of application No. 13/695,458, filed as application No. PCT/FR2011/050953 on Apr. 27, 2011, now Pat. No. 9,085,635.

(30) Foreign Application Priority Data

Apr. 27, 2010 (FR) ...................................... 1053225

(51) Int. Cl.
| | |
|---|---|
| *C07K 14/47* | (2006.01) |
| *A61Q 19/00* | (2006.01) |
| *A61Q 19/08* | (2006.01) |
| *C07K 7/08* | (2006.01) |
| *A61K 8/64* | (2006.01) |
| *C07K 7/06* | (2006.01) |
| *A61K 38/00* | (2006.01) |

(52) U.S. Cl.
CPC ............ *C07K 7/08* (2013.01); *A61K 8/64* (2013.01); *A61Q 19/007* (2013.01); *A61Q 19/08* (2013.01); *C07K 7/06* (2013.01); *C07K 14/47* (2013.01); *A61K 38/00* (2013.01)

(58) Field of Classification Search
CPC ........ A61K 38/00; A61K 8/64; A61Q 19/007; A61Q 19/08; C07K 14/47; C07K 7/06; C07K 7/08
See application file for complete search history.

(56) References Cited

U.S. PATENT DOCUMENTS

2003/0113322 A1* 6/2003 Bes .................... C07K 16/2812
424/144.1
2004/0137434 A1 7/2004 Tang et al.

FOREIGN PATENT DOCUMENTS

| EP | 1342474 | 9/2003 |
|---|---|---|
| WO | WO 9308816 | 5/1993 |
| WO | 96/40780 | 12/1996 |
| WO | 02/07707 | 1/2002 |
| WO | 02/059260 | 8/2002 |
| WO | 2008/016356 | 2/2008 |

OTHER PUBLICATIONS

Merriam Webster Dictionary, Definition of Prevent, accessed on Nov. 25, 2020, pp. 1-11.*
"RECNAME : Full=Late Cornified Envelope Protein 6A"; Nov. 14, 2006; XP002604655.
*Homo Sapiens* Late Cornified Envelope 6A; Oct. 20, 2006; XP002604656.
Marshall et al..; "Differentially Expressed Late Constituents of the Epidermal Cornified Envelope"; PNAS; vol. 98, No. 23, Nov. 6, 2001; pp. 13031-13036; XP002604657.
De Cid et al.; "Deletion of the Late Cornified Envelope LCE3B and LCE3C Genes as a Susceptibility Factor for Psoriasis"; Nature Genetics; vol. 41, No. 2; Feb. 2009; pp. 211-215; XP002604658.
Rudinger, Peptide Hormones, JA Parsons, Ed., 1976, pp. 1-7.
Sigma, 2004, pp. 1-2.
Berendsen, A Glimpae of the Holy Grail?, Science, 1998, 282, pp. 642-643.
Voet et al., Biochemistry, John Wiley & Sons Inc., 1995, pp. 235-241.
Ngo et al., Computational Complexity, Protein Structure Protection, and the Levinthal Paradox, 1994, pp. 491-494.
Bradley et al., Limits of Cooperativity in a Structurally Modular Protein: Response of the Notch Ankyrin Domain to Ana Alanine Substitutions in Each Repeat, J. Mol. BloL (2002) 324, 373-386.

(Continued)

*Primary Examiner* — Julie Ha
*Assistant Examiner* — Erinne R Dabkowski
(74) *Attorney, Agent, or Firm* — Nixon & Vanderhye

(57) ABSTRACT

Polypeptides belonging to the family of late proteins of the cornified envelope (LCE), fragments of the polypeptide, isolated nucleotide sequences encoding the polypeptides, and cosmetic and/or pharmaceutical compositions containing such polypeptides are described. The polypeptides have cosmetic and/or therapeutic use to reinforce the barrier function of the epidermis, prevent and/or treat the signs of skin dryness and prevent and/or treat disorders of the barrier function or the weakening of the epidermis.

2 Claims, 1 Drawing Sheet
Specification includes a Sequence Listing.

(56) References Cited

OTHER PUBLICATIONS

The On-line Medical Dictionary. http://cancerweb.ncl.ac.uk/omd/index.html.Jul. 7, 2005.
Human Late Cornified Envelope Protein 6A, UniProtKB/Swiss-Prot, Accession A0A183 (LCE6A_Human), Nov. 14, 2006.
Shakhashiri, www.scifun.org, Chemical of the Week, Water, pp. 1-7, accessed on May 17, 2014.
Uniprot Protein Database, Protein Accession E0VTN7, accessed on May 16, 2018.
George B. Stroup,Potent and Selective Inhibition of Human Cathepsin K. Leads to Inhibition of Bone Resorption In Vivo in a Nonhuman Primate, (J Bone Miner Res 2001;16:1739-1746), 2001.

* cited by examiner

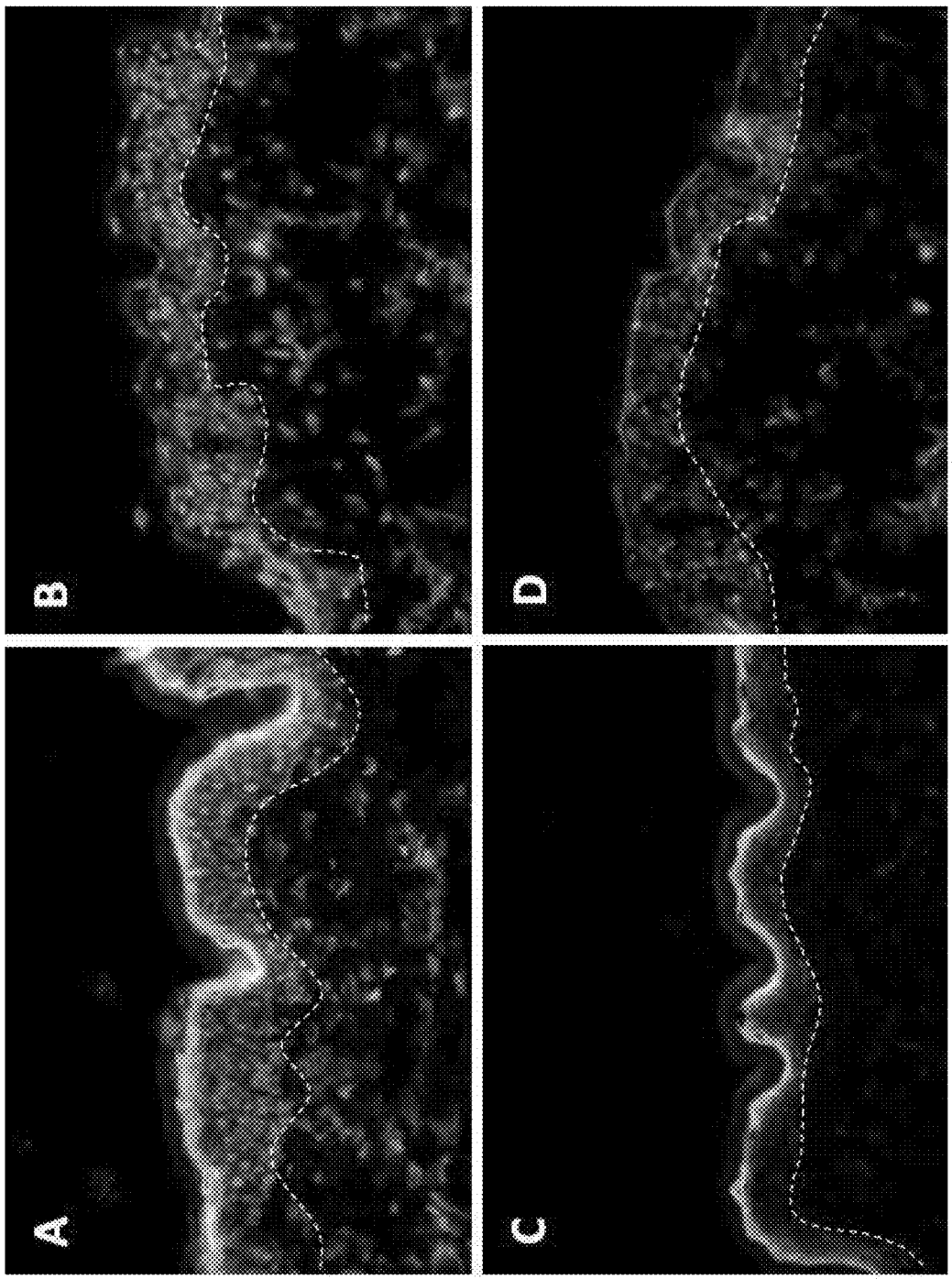

POLYPEPTIDE EXPRESSED IN THE STRATUM CORNEUM AND USE THEREOF

FIELD OF THE INVENTION

The present invention relates to a novel polypeptide of the stratum corneum, designated LCE6A hereinafter, as well as to applications thereof, both cosmetic and therapeutic.

BACKGROUND OF THE INVENTION

The skin consists mainly of three layers, namely, starting from the outermost: epidermis, dermis and hypodermis.

The epidermis consists in particular of keratinocytes (primarily), melanocytes (involved in skin pigmentation) and Langerhans cells. Its function is to protect the body from the external environment and ensure its integrity, and notably to block the penetration of microorganisms or of chemical substances, and prevent evaporation of the water contained in the skin.

For this purpose, the keratinocytes undergo a continuous process of directed maturation, in which the keratinocytes located in the basal layer of the epidermis form, in the terminal stage of their differentiation, corneocytes, which are cells resulting from cornification (a particular form of apoptosis). These corneocytes are very inter-cohesive, fully keratinized in the form of cornified envelopes and surrounded by an extracellular medium that is very rich in lipids. The constituent elements of these cells, as well as the enzymes that regulate their detachment to permit desquamation, are mainly synthesized by the keratinocytes of the underlying cellular layer, the stratum granulosum or granular layer. The granular keratinocytes correspond to the last nucleated stage of keratinocyte differentiation, before cornification, which is accompanied by nuclear lysis with stoppage of all activity of transcription and translation. It is at this stage that there is culmination of the production of the precursors of the cornified envelope and other specific cellular constituents indispensable to the barrier function of the epidermis such as ceramides, cholesterol and free fatty acids. The cornified envelope formed during cornification replaces the lipid bilayer of granular keratinocytes. It represents 7% of the dry weight of the stratum corneum. It consists of proteins that are bound to one another or to the lamellar lipid envelope covalently by transglutaminases, forming a macromolecular complex that is particularly stable, insoluble and impermeable, which is essential for the physical strength and the barrier function of the stratum corneum.

Epidermal differentiation is a complex phenomenon requiring fine regulation of the expression of the genes permitting manufacture of the various constituents of the keratinocytes and then of the corneocytes. A great many transcription factors are involved in this process. The genes of numerous proteins of the cornified envelope are localized within one and the same cluster of 2.5 Mb called the "Epidermal Differentiation Complex" (EDC) in position 1q21.3. The EDC comprises more than 50 different genes, expressed principally in the epidermis. Most of the genes coding for the structural proteins necessary for terminal differentiation, such as loricrin, filaggrin and involucrin, are found there. The EDC also contains several families of genes, at least 18 of which code for the late proteins of the Late Cornified Envelope (LCE) (Marshall et al. 2001, Differentially expressed late constituents of the epidermal cornified envelope. *Proc Natl Acad Sci USA*. 98: 13031-6). In the course of cornification, these proteins of the LCE family are incorporated in the cornified envelope owing to the action of transglutaminases, which establish an ε-(γ-glutamyl) lysyl linkage between a donor glutamine residue and an acceptor amine group, in a calcium-dependent manner.

The barrier function of the epidermis may be disturbed in certain climatic conditions (under the effect of cold and/or wind, for example); under the effect of stress or fatigue; under the effect of certain chemical factors (pollution, ultraviolet radiation, alcohol, irritating soaps, domestic cleaning products, detergents, etc.).

Many skin disorders that are characterized by production of a thickened stratum corneum and by abnormal desquamation, i.e. hyperkeratosis, also display an altered barrier function. Hyperkeratosis can occur on all anatomic skin areas and in very varied clinical contexts. Its underlying physiopathology and its causes are varied. As examples we may mention: xerosis (or dry skin), ichthyoses, psoriasis, certain benign or malignant tumoral lesions, reactive hyperkeratoses. Conversely, certain pathological manifestations involve thinning of the epidermis and especially of the stratum corneum, which is reflected in excessive fragility of the skin. The latter can occur in various anatomical regions, its cause is variable and it can be constitutional or acquired. As examples we may mention: trophic skin disorders of the lower limbs in patients with vascular disorders, varices, arteriopathies (diabetes, arteriosclerosis, etc.), trophic skin disorders in the context of an algodystrophic syndrome, trophic disorders following abnormal healing.

The barrier function of the epidermis may also be disturbed during aging. Thus, older subjects, and notably those over 50 years of age, are often found to have a xerosis or a dryness of the mucosae, linked to a decrease in secretion of sebum, hormonal changes or to slowing of the flow of water through the epidermis. These disturbances of the barrier of the epidermis cause a decrease in the amount of organized water, a desynchronization of the synthesis or a change in the structure and/or composition of the bilayers of the granular layer. These changes thus promote desquamation of the stratum corneum, penetration of allergens, of irritants or of microorganisms, which thus cause dry skin, which may give rise to sensations of discomfort such as tightness or redness, as well as affecting the radiance of the complexion and the flexibility of the skin.

To prevent this phenomenon or correct it, it is known to apply cosmetic or pharmaceutical compositions on the skin, said compositions containing hygroscopic agents, such as sugars or polyols, or urea and lactic acid (components of the NMF, Natural Moisturizer Factor) intended to capture the water present in the skin and thus block its evaporation. Classically, fats have also been used for forming an occlusive film on the skin, such as petroleum jelly, which helps to block the evaporation of water. Moreover, these compositions frequently incorporate active ingredients acting on one or more of the various biological targets involved either in the processes of regeneration of the skin, in particular in the differentiation of the keratinocytes, synthesis of the epidermal lipids and cohesion of the corneocytes, or in the endogenous synthesis of constituents of the natural moisturizer factor (NMF) of the skin, in particular in the synthesis of proteoglycans.

However, there is still a need for new cosmetic or pharmaceutical active ingredients for more effectively combating dry skin, disorders of the barrier function and/or development of fragility of the epidermis.

SUMMARY OF THE INVENTION

Now, following the analysis of the transcriptome of the human granular keratinocyte that was performed by the applicant (Toulza et al., Large-scale identification of human genes implicated in epidermal barrier function, *Genome Biology* 2007, 8: R107), the applicant identified a new gene located in the EDC on human chromosome 1q21, coding for a polypeptide of 80 amino acids, which it decided to designate as LCE6A, and whose complementary DNA has been isolated and cloned (Human Gene Nomenclature, GenBank DQ991251).

Based on the sequence of the gene corresponding to this novel LCE6A protein, with a length of 1130 kb, it can be asserted that it belongs to the "Late Cornified Envelope" (LCE) family, a family of genes coding for proteins of the cornified envelope. The expression of this gene is very strongly induced in the fraction that is rich in granular keratinocytes, which corresponds to a late stage of keratinocyte differentiation. Although belonging to the LCE family, the polypeptide sequence corresponding to LCE6A displays little homology with the sequences of the other proteins of this same family and constitutes a new group among the 5 groups currently known in the LCE family.

The polypeptide sequence of the LCE6A protein is of 80 amino acids. It contains 8 glutamine residues and 6 lysine residues. Among a panel of 17 human complementary DNAs of healthy tissues or organs (heart, brain, placenta, lung, liver, muscle, kidney, pancreas, spleen, thymus, prostate, testis, ovary, small intestine, colon, leukocytes, epidermis), expression of the LCE6A gene was only found in the epidermis.

Consequently, according to one aspect, the present invention relates to a natural or synthetic isolated polypeptide, said polypeptide belonging to the family of late proteins of the cornified envelope (LCE), said polypeptide being selected from:
  the sequence SEQ ID NO: 2,
  fragments of SEQ ID NO: 2, said fragments having at least one glutamine (Gln)-lysine (Lys) domain, and
  analogs of SEQ ID NO: 2 or of one of its fragments, said analogs having at least one glutamine (Gln)-lysine (Lys) domain.

According to another aspect, the present invention relates to a cosmetic or nontherapeutic use, of an effective amount:
  of at least one polypeptide selected from the sequence SEQ ID NO: 2, fragments of SEQ ID NO: 2, and analogs of SEQ ID NO: 2 or of one of its fragments, said fragments and analogs having at least one glutamine (Gln)-lysine (Lys) domain and/or
  of at least one polypeptide of sequence encoded by a nucleic acid sequence selected from the sequence SEQ ID NO: 1, fragments of SEQ ID NO: 1 and analogs of SEQ ID NO: 1 or of one of its fragments, and/or
  of at least one nucleotide sequence coding for said polypeptide,
as an agent useful for reinforcing the barrier function of the epidermis and/or preventing and/or treating the signs of dry skin and/or preventing and/or treating the signs of skin aging.

According to another aspect, the present invention also relates to the use:
  of at least one polypeptide selected from the sequence SEQ ID NO: 2, fragments of SEQ ID NO: 2, and analogs of SEQ ID NO: 2 or of one of its fragments, said fragments and analogs having at least one glutamine (Gln)-lysine (Lys) domain and/or
  of at least one polypeptide of sequence encoded by a nucleic acid sequence selected from the sequence SEQ ID NO: 1, fragments of SEQ ID NO: 1, and analogs of SEQ ID NO: 1 or of one of its fragments, and/or
  of at least one nucleotide sequence coding for said polypeptide,
for manufacturing a therapeutic composition intended for:
  reinforcing the barrier function of the epidermis and preventing and/or treating the signs of dry skin or preventing and/or treating the signs of skin aging; and/or
  preventing and/or treating trophic skin disorders or those following disorders of healing; and/or
  preventing and/or treating thinning of the epidermis and in particular of the stratum corneum and/or for treating excessive fragility of the skin and/or for inducing thickening of the stratum corneum; and/or
  treating hyperkeratosis, xerosis, ichthyoses, psoriasis, benign or malignant hyperkeratotic tumoral lesions or reactive keratoses.

The present invention also relates to one of the polypeptides described above for use for preventing and/or treating the aforementioned disorders.

According to another of its aspects, the present invention also relates to a cosmetic or pharmaceutical composition comprising, in a physiologically acceptable medium, at least one natural or synthetic isolated polypeptide, said polypeptide comprising at least the amino acid sequence represented by SEQ ID NO: 2, or a fragment of the latter, or an analog of SEQ ID NO: 2 or of one of its fragments, said fragments and analogs having at least one glutamine (Gln)-lysine (Lys) domain.

According to another aspect, the present invention also relates to an isolated polynucleotide comprising at least the sequence SEQ ID NO: 1, said polynucleotide coding for a polypeptide comprising the amino acid sequence represented by SEQ ID NO: 2, a fragment of SEQ ID NO: 1, or an analog of SEQ ID NO: 1 or of one of its fragments.

BRIEF DESCRIPTION OF THE FIGURES

FIG. 1: Represents in vitro crosslinking binding assay with peptide PEVQKG (SEQ ID NO: 10), having more than 80% homology with peptide PEVQKP (SEQ ID NO: 15) of LCE6A and one glutamine (Gln, Q)-Lysine (Lys, K) domain.

DETAILED DESCRIPTION OF THE INVENTION

"Reinforcing the barrier function of the skin" means ensuring that the barrier function of the skin is maintained at a minimum level of effectiveness corresponding to its normal level of effectiveness, i.e. the level at which it performs its function of protecting the body.

"Signs of dry skin" means all the changes in the outward appearance of the skin due notably to dehydration of the epidermis, such as dull, rough, nonsilky, reddish and/or scaly appearance, as well as loss of flexibility and a decrease in thickness of the skin. In severe cases, the signs of dry skin include the sensations associated with the phenomenon of dryness, such as itching, tingling and/or tightness, which can lead to the development of actual disorders, such as hypersensitivity, skin atrophy, atopic dermatitides or winter xeroses.

"Preventing and/or treating the signs of dry skin" consequently means reinforcing, preserving and/or restoring the epidermal barrier, notably its protective or regulatory function, improving and/or reinforcing the cellular cohesion of the epidermis, increasing epidermal resistance to aggressive agents, improving and/or reinforcing the structure of the epidermis, increasing its thickness, and/or guaranteeing the integrity of the skin.

"Preventing and/or treating the signs of skin aging" preferably means light-induced aging or photo-aging. "Signs of skin aging" means all the changes of the outward appearance of the skin due to aging, for example wrinkles and lines, withered skin, soft skin, thin skin, lack of elasticity and/or firmness of the skin, dull skin without radiance.

"Effective amount", in the sense of the present invention, means the minimum amount necessary for observing the expected effect, namely a cosmetic effect or a therapeutic effect, it being understood that the effective amounts required for obtaining a cosmetic effect or a therapeutic effect may be identical or different, depending on circumstances.

"Trophic skin disorders" means disorders that are notably of vascular origin, abnormalities of the skin (epidermis, dermis and hypodermis) or lesions caused by microcirculatory insufficiency of arterial or venous origin. They are called trophic disorders because they result from poor nutrition of the skin, which is poorly perfused.

Polypeptides According to the Invention

"Polypeptide" means a molecule comprising a linear chain of amino acids that are joined to one another by peptide bonds.

In the present description, the term polypeptide will also be used for denoting a protein or a peptide.

The polypeptides according to the invention have a length less than or equal to 80 amino acids. Preferably, the polypeptide consists of 4 to 20, more preferably 7 to 15 amino acids.

One of the essential characteristics of this polypeptide is that it must have at least one glutamine (Q, Gln)-lysine (K, Lys) domain so that it can serve as a substrate for the transglutaminases.

According to the invention, the polypeptide is selected from the amino acid sequence SEQ ID NO: 2, the fragments of SEQ ID NO: 2 and the analogs of SEQ ID NO: 2 or of its fragments, said fragments and analogs having at least one glutamine (Gln)-lysine (Lys) domain.

Examples of analogs of SEQ ID NO: 2 fragments are analogs of:
  fragment PEVQKP (SEQ ID NO: 15) which corresponds to the amino-acids 49 to 54 of SEQ ID NO: 2. Such analogs have e.g. the amino-acid sequence PGVQKP (SEQ ID NO: 7), PEGQKP (SEQ ID NO: 8), GEVQKP (SEQ ID NO: 9), PEVQKG (SEQ ID NO: 10);
  fragments of SQQKQQS (SEQ ID NO: 16) which corresponds to amino-acids 2 to 8 of SEQ ID NO: 2. Such analogs have e.g. the amino-acid sequence QKQTS (SEQ ID NO: 11), STQKQ (SEQ ID NO: 12), SQQKT (SEQ ID NO: 13), and QKTQS (SEQ ID NO: 14).

In the sense of the present invention, LCE6A is generally intended to denote, unless stated otherwise, the sequence SEQ ID NO: 2 of the protein, which may or may not have undergone post-translational modifications.

The polypeptide according to the invention is an isolated polypeptide. "Isolated" polypeptide means a polypeptide isolated from the human body or from a living organism, preferably in purified form.

"Analog of a polypeptide" is intended to denote any polypeptide having (a) a homology of amino acid sequence, in particular with respect to one of the sequences characteristic of said polypeptide or of its fragments, as well as (b) a biological activity of the same nature. The homology can be at least 80%, for example at least 85%, and for example at least 95%. This sequence homology can result from changes due to one or more mutations (substitutions, insertions or deletions) in the sequences of the polypeptides according to the invention. Preferably, said polypeptides comprise only mutations of the substitution type. These substitutions can be conservative or not. Percentage homology means the number of identical residues between two sequences, said sequences being aligned so as to obtain maximum correspondence. Various algorithms known from the prior art can be used for measuring the homology between two sequences. For example, polynucleotide sequences can be compared using FASTA, Gap or Bestfit, which are programs from Wisconsin Package Version 10.0, Genetics Computer Group (GCG), Madison, Wis. Alternatively, the sequences can be compared using the BLAST program (Altschul et al., J. Mol. Biol. 215: 403-410 (1990); Gish and States, Nature Genet. 3: 266-272 (1993); Madden et al., Meth. Enzymol. 266: 131-141 (1996); Altschul et al., Nucleic Acids Res. 25: 3389-3402 (1997); Zhang and Madden, Genome Res. 7: 649-656 (1997)), in particular blastp or tblastn (Altschul et al., Nucleic Acids Res. 25: 3389-3402 (1997)).

"Biological activity of the same nature" denotes in particular an analog or a fragment of amino acid sequence of polypeptide according to the invention having at least one of the functional characteristics or properties of the polypeptides according to the invention, notably in that: (i) it is capable of being recognized by a specific antibody of a polypeptide according to the invention; (ii) it has at least one of the domains or regions as defined below; (iii) it is capable of binding the transglutaminases (TGM) such as human TGM 1, 3 and 5 that participate in the formation of the cornified envelope.

According to a preferred embodiment, the analog of the polypeptide according to the invention differs from the sequence of the LCE6A protein (SEQ ID NO: 2) only by the presence of conservative substitutions. As examples of conservative mutations that can be considered in the present invention, we may mention, nonexhaustively, replacement of one or more amino acid residues with amino acids of the same class, such as substitutions of amino acids on the uncharged side chains (such as asparagine, glutamine, serine, cysteine and tyrosine), of amino acids on the basic side chains (such as lysine, arginine, and histidine), of amino acids on the acidic side chains (such as aspartic acid and glutamic acid), of amino acids on the nonpolar side chains (such as alanine, valine, leucine, isoleucine, proline, phenylalanine, methionine and tryptophan).

The present invention also relates to a polypeptide or analog that can be a polypeptide that has undergone one or more post-translational modification(s).

The term "post-translational modification(s)" is intended to comprise all the modifications that a polypeptide can undergo following its synthesis in a cell, such as, for example, one or more phosphorylation(s), one or more thiolation(s), one or more acetylation(s), one or more glycosylation(s), one or more lipidation(s), such as a palmitoylation, a structural rearrangement of the type of formation of disulfide bridges within the peptide sequence.

In the sense of the invention, "polypeptide fragment" is intended to denote any portion of a polypeptide according to the invention comprising at least 5, preferably at least 7, preferably at least 9, and more particularly at least 15 consecutive amino acids of said polypeptide, said portion having, in addition, a biological activity of the same nature.

According to a preferred embodiment, a polypeptide fragment suitable for the invention is selected from the sequences SEQ ID NO: 3, SEQ ID NO: 4, SEQ ID NO: 5, and mixtures thereof.

According to another embodiment, a polypeptide suitable for carrying out the invention is also a polypeptide as defined above, fused with another polypeptide, a hydrophilic or hydrophobic targeting agent, a bioconversion precursor, a luminescent, radioactive or colorimetric labeling agent. Non-exhaustively, as examples of compounds that can be coupled to a polypeptide according to the invention we may mention fluorescent proteins, fluorescent chemicals such as rhodamine, fluorescein, phosphorescent compounds, radioactive elements or colorimetric labeling agents such as chromogenic substrates that are sensitive to the action of certain enzymes such as galactosidase, peroxidase, acetyltransferase.

Depending on the nature of the compounds that can be coupled to a polypeptide according to the invention, the coupling can be performed by chemical methods, notably by means of reactive chemical functions or by methods of molecular biology known by a person skilled in the art.

The polypeptide according to the invention can further comprise one or more chemical modification(s) that improve its resistance to degradation or its bioavailability. This modification must be biologically compatible and must be compatible with use in the area of cosmetics or pharmacy. These chemical or enzymatic modifications are well known by a person skilled in the art. Non-exhaustively, we may mention for example: modifications of the C- or N-terminal ends of the polypeptides (acetylation); modifications of the bond between two amino acids (acylation or alkylation); changes of chirality. Preferably, protection is used that is based either on acylation or acetylation of the amino-terminal end, or on amidation or esterification of the carboxy-terminal end, or both.

Thus, the invention relates to a polypeptide as defined above, said polypeptide being in protected or unprotected form.

In the area of amino acids, the geometry of the molecules is such that they can theoretically be in the form of different optical isomers. There is, in fact, a molecular conformation of the amino acid (AA) such that it rotates the plane of polarization of light to the right (dextrorotatory conformation or D-aa), and a molecular conformation of the amino acid (aa) such that it rotates the plane of polarization of light to the left (laevorotatory conformation or L-aa). For natural amino acids, nature has only adopted the laevorotatory conformation. Consequently, a polypeptide of natural origin will only be constituted of amino acids of the L-aa type. However, chemical synthesis in the laboratory makes it possible to prepare amino acids having both possible conformations. Starting from this base material, it is thus also possible to incorporate, during polypeptide synthesis, amino acids in the form of dextrorotatory or laevorotatory optical isomers.

Thus, the amino acids constituting the polypeptide according to the invention can be in L- and D-configuration; preferably, the amino acids are in the L form. The polypeptide according to the invention can therefore be in the L-, D- or DL-form.

The polypeptides according to the invention can be of natural or synthetic origin. They can be synthesized by any method well known by a person skilled in the art. Such methods notably include classical chemical synthesis (in solid phase or in liquid homogeneous phase), enzymatic synthesis (Kullman et al., J. Biol. Chem. 1980, 225, 8234) from constitutive amino acids or derivatives thereof.

The polypeptides according to the invention can also be obtained by methods of biological production such as fermentation of a strain of modified or unmodified bacteria, by genetic engineering to produce the polypeptides or fragments according to the invention using recombinant techniques (cf. examples), or by extraction of proteins of animal or vegetable origin followed by controlled hydrolysis that liberates the medium-sized and small peptide fragments according to the invention. Other simpler or more complex methods can be envisaged by a person skilled in the art familiar with the synthesis, extraction and purification of proteins and of peptides.

Preferably, the polypeptides according to the invention are obtained by chemical synthesis, this technology being particularly advantageous for reasons of purity, antigen specificity, absence of undesirable reaction byproducts and for its ease of production.

According to an advantageous embodiment of the invention, the aforementioned polypeptides according to the invention are first dissolved in one or more cosmetically or pharmaceutically acceptable solvents. Such solvents are used conventionally by a person skilled in the art, such as water, glycerol, ethanol, propylene glycol, butylene glycol, dipropylene glycol, ethoxylated or propoxylated diglycols, cyclic polyols, petroleum jelly, a vegetable oil or any mixture of these solvents.

According to another advantageous embodiment of the invention, the aforementioned polypeptides are first dissolved in a cosmetic or pharmaceutical carrier such as liposomes or adsorbed on powdered organic polymers, mineral supports such as talcs and bentonites, and more generally dissolved in, or fixed on, any cosmetically or pharmaceutically acceptable carrier.

The Nucleic Acid Sequence According to the Invention

According to one embodiment, the present invention also relates to nucleic acid sequences coding for a polypeptide of the invention and application thereof in the various uses according to the invention.

The term "nucleic acid" denotes a chain (strands) of at least two deoxyribonucleotides or ribonucleotides optionally comprising at least one modified nucleotide permitting hybridization, comprising for example a modified bond, a modified purine or pyrimidine base, or a modified sugar.

The nucleic acid can be deoxyribonucleic acid (DNA) or ribonucleic acid (RNA), or a mixture of the two. It can be in the form of a single chain (single-stranded) or double chain (double-stranded), or a mixture of the two.

Thus, the present invention also relates to the use of nucleic acid sequences coding for a polypeptide according to the invention, notably the sequences corresponding at least to a nucleic acid sequence represented by SEQ ID NO: 1, analogs of the latter or a fragment of the latter for preparing a composition according to the invention.

In the sense of the present invention, "fragment of nucleic acid sequence" means a nucleic acid sequence coding for a part of a polypeptide according to the invention, or an analog of the latter, and in particular a sequence represented by SEQ ID NO: 1 or an analog of the latter.

"Analog of a nucleic acid sequence" means any nucleic acid sequence, optionally resulting from the degeneration of the nucleic acid code, and coding for a polypeptide of sequence identical or similar to that of the polypeptide encoded by said nucleic acid sequence.

The nucleic acid can be natural or synthetic, an oligonucleotide, a polynucleotide, a fragment of nucleic acid, a messenger RNA, a nucleic acid obtained by a technique of enzymatic amplification such as PCR (Polymerase Chain Reaction).

The nucleic acid sequences can be derived from all possible origins, namely either animal, in particular mammalian and even more particularly human, or vegetable, or from microorganisms (viruses, phages, bacteria among others) or from fungi, without prejudging whether or not they are present naturally in said original organism.

According to a preferred embodiment, the polynucleotides according to the invention can be used as primer and/or probe in methods notably employing the PCR technique.

This technique requires choosing pairs of oligonucleotide primers flanking the fragment that is to be amplified. The amplified fragments can be identified, for example after agarose or polyacrylamide gel electrophoresis, or after a chromatographic technique such as gel filtration or ion exchange chromatography. The specificity of amplification can be controlled by molecular hybridization using, as probe, the nucleotide sequences of polynucleotides of the invention, plasmids containing these sequences or amplification products thereof.

The amplified nucleotide fragments can be used as reagents in hybridization reactions for detecting the presence, in a biological sample, of a target nucleic acid with sequence complementary to that of said amplified nucleotide fragments.

The invention also relates to the nucleotide fragments obtainable by amplification using primers according to the invention.

Other techniques for amplification of the target nucleic acid can be used advantageously as an alternative to PCR (PCR-like) using primer pairs with nucleotide sequences according to the invention. PCR-like will denote all methods using direct or indirect reproduction of nucleic acid sequences, or else in which the labeling systems have been amplified, these techniques are of course known, in general it is a matter of amplifying DNA by a polymerase; if the original sample is an RNA, a reverse transcription should be carried out first.

In the case when the target polynucleotide to be detected is an RNA, for example an mRNA, it will be advantageous to use, prior to application of a reaction of amplification by means of the primers according to the invention or to application of a method of detection by means of the probes of the invention, an enzyme of the reverse transcriptase type in order to obtain a complementary DNA (cDNA) from the RNA contained in the biological sample. The cDNA obtained will then serve as target for the primers or the probes employed in the method of amplification or of detection according to the invention.

In that case, the invention also relates to the use of isolated and purified nucleic acid fragments coding for the polypeptides considered according to the invention.

A nucleic acid sequence according to the invention can comprise a sense, antisense or interference sequence corresponding to a sequence coding for a polypeptide according to the invention.

Thus, the present invention also relates to the use of sequences of nucleic acids, notably of deoxyribonucleic acids, or of ribonucleic acids, coding for a polypeptide according to the invention. The nucleic acid sequences according to the invention can notably be used for preparing sequences of corresponding, sense or antisense ribonucleic acids.

The invention also relates to the use of a polynucleotide of ribonucleic acid or deoxyribonucleic acid sequence comprising a sense or antisense sequence, notably "small interfering RNA" (siRNA) corresponding at least to the nucleic acid sequence SEQ ID NO: 1 or an analog of the latter.

The amount of polypeptide or of nucleic acid sequence according to the invention contained in a composition according to the invention, also called "effective amount", is of course a function of the nature of the compound and of the required effect and can therefore vary widely. To give an order of magnitude, a composition can contain a polypeptide or a nucleic acid sequence according to the invention in an amount representing from 0.00001% to 20% of the total weight of the composition, in particular in an amount representing from 0.0001% to 5% of the total weight of the composition, and more particularly in an amount representing from 0.003% to 3% of the total weight of the composition.

The Composition According to the Invention

Preferably, the composition according to the invention is applied on pathological or nonpathological dry skin. It can advantageously be applied on the skin of the face, neck and optionally of the cleavage or as a variant on any part of the body.

The cosmetic and/or pharmaceutical composition can be applied in the morning and/or in the evening, on all of the face, of the neck and optionally of the cleavage or even of the body.

The cosmetic and/or pharmaceutical composition employed according to the invention generally comprises a physiologically acceptable and preferably cosmetically acceptable medium, i.e. it is suitable for use in contact with human skin without risk of toxicity, incompatibility, instability, allergic reaction and notably does not cause sensations of discomfort (redness, tightness, tingling, etc.) that are unacceptable for the user.

Preferably, the physiologically acceptable medium consists of water.

The cosmetic and/or pharmaceutical composition used according to the invention can be in any form that is suitable for topical application on the skin and in particular in the form of oil-in-water, water-in-oil or multiple (W/O/W or O/W/O) emulsion, which can optionally be microemulsions or nanoemulsions, or in the form of aqueous dispersion, solution, aqueous gel or powder. Preferably, said composition is in the form of an oil-in-water emulsion.

This composition, when used as a care or cleaning product for the skin of the face and/or of the body, can notably be in the form of fluid, gel or mousse, packaged for example in a pump-action spray bottle, an aerosol or a tube, or cream packaged for example in a pot. As a variant, it can be in the form of a makeup product and in particular a foundation or a loose or compacted powder.

Besides the polypeptide described above, the cosmetic and/or pharmaceutical composition according to the invention can also comprise at least one additive that is usual in the area of cosmetics or pharmacy, for example a compound selected from a gelling agent and/or thickener, a surfactant or co-surfactant, a liquid fat or an oil, a wax, a silicone elastomer, a sun filter, a dye, a matting agent or a filler, a pigment, a lifting agent, a preservative, a sequestering agent, a perfume and mixtures thereof.

Notably, according to a preferred embodiment, the cosmetic composition according to the invention can comprise, nonexhaustively, one or more of the following additives:
one or more gelling agent(s) and/or thickener(s) of the aqueous phase, selected for example from crosslinked or noncrosslinked, hydrophilic or amphiphilic homo- and copolymers of acryloylmethylpropane sulfonic acid (AMPS) and/or of acrylamide and/or of acrylic acid and/or of salts or of esters of acrylic acid such as ammonium acryloyldimethyltaurate/VP copolymer and ammonium acryloyldimethyltaurate/beheneth-25 methacrylate copolymer, notably those sold under the names Aristoflex® AVC and HMB from Clariant, or the acrylates/C10-30 Alkyl Acrylate Crosspolymers sold under the trade name PEMULEN® TR-1 or TR-2, Carbopol® 1382, Carbopol® Ultrez by the company Novéon, cellulose derivatives, gums of vegetable origin (gum acacia or gum arabic, agar, guar, carob, alginates, carrageenans, pectin) or of microbial origin (xanthan, pullulan), clays (laponite). Said gelling agent and/or thickener can be present in the composition at a content of the order of 0.01 to 5 wt %, relative to the total weight of the composition;

one or more surfactant(s), preferably emulsifiers, whether nonionic, anionic, cationic or amphoteric, and in particular the esters of fatty acids and of polyols such as the alkoxylated (more particularly polyethoxylated) esters of fatty acids and of glycerol, the alkoxylated esters of fatty acids and of sorbitan, the alkoxylated (ethoxylated and/or propoxylated) esters of fatty acids such as the mixture PEG-100 Stearate/Glyceryl Stearate marketed for example by the company Croda under the name Arlacel® 165 and the esters of fatty acids and of sucrose such as sucrose stearate; the ethers of fatty alcohol and of sugar, notably the alkylpolyglucosides (APG) such as decylglucoside and laurylglucoside, ketostearylglucoside optionally mixed with ketostearyl alcohol, marketed for example under the name Montanov® 68 by the company Seppic, as well as arachidyl glucoside, for example in the form of the mixture of arachidic and behenic alcohols and of arachidylglucoside marketed under the name Montanov® 202 by the company Seppic; ethers of fatty alcohols and of polyethyleneglycol; the polysiloxanes modified polyethers; betaine and derivatives thereof; the polyquaterniums; the ethoxylated sulfate salts of fatty alcohols; the sulfosuccinates; sarcosinates; alkyl- and dialkylphosphates and salts thereof; and the soaps of fatty acids. Said surfactant can be present in the composition at a content of the order of 0.1 to 8%, preferably 0.5 to 3 wt %, relative to the total weight of the composition;

one or more co-surfactant(s) such as the linear fatty alcohols with a long carbon chain (C14-C20) and in particular cetyl and stearyl alcohols, said surfactant being present in the composition at a rate from 0.1 to 5 wt %, preferably 0.5 to 2 wt %, relative to the total weight of the composition;

one or more fats that are liquid at room temperature, commonly called oils(s), volatile or nonvolatile, hydrocarbon, silicone, linear, cyclic or branched, for example silicone oils such as polydimethylsiloxanes (dimethicones), polyalkylcyclosiloxanes (cyclomethicones) and polyalkylphenylsiloxanes (phenyldimethicones); synthetic oils such as fluorinated oils, alkyl benzoates and branched hydrocarbons such as polyisobutylene, isododecane; mineral oils (paraffin); vegetable oils (sweet almond oil, macadamia oil, blackcurrant seed oil, jojoba oil or oil of Camelina sativa such as the oil sold under the trade name Lipex® Omega 3/6 by the company Unipex); fatty alcohols, fatty amides, fatty acids or esters such as the benzoate of C12-C15 alcohols sold under the trade name Finsolv® TN by the company Innospec, triglycerides including those of capric/caprylic acids, dicaprylyl carbonate sold under the name Cetiol® CC by the company Cognis; preferably at a rate from 0.1 to about 10 wt %, preferably from 0.5 to 5 wt %, relative to the total weight of the composition;

one or more waxes (compounds that are solid or substantially solid at room temperature), and whose melting point is generally above 35° C., such as ozokerite, polyethylene wax, beeswax or carnauba wax, preferably at a rate from 0.01 to about 5 wt %, preferably 0.5 to 5 wt %, relative to the total weight of the composition;

one or more silicone elastomer(s) obtained notably by reaction, in the presence of a catalyst, of a polysiloxane having at least one reactive group (hydrogen or vinyl, notably) and bearing at least one alkyl (notably methyl) or phenyl end group or side group, with an organosilicone such as an organohydrogen-polysiloxane, preferably at a rate from 0.1 to about 20 wt %, preferably 0.25 to 15 wt %, relative to the total weight of the composition;

one or more sun filters, notably organic filters, such as derivatives of dibenzoylmethane (including butyl methoxydibenzoylmethane sold in particular by DSM under the trade name Parsol® 1789), derivatives of cinnamic acid (including ethylhexyl methoxycinnamate sold in particular by DSM under the trade name Parsol® MCX), salicylates, para-aminobenzoic acids, β-β-diphenylacrylates, benzophenones, derivatives of benzylidene camphor, phenylbenzimidazoles, triazines, phenylbenzotriazoles and anthranilic derivatives; or inorganic filters, based on mineral oxides in the form of pigments or of nanopigments, coated or uncoated, and in particular based on titanium dioxide or zinc oxide; preferably at a rate from 0.1 to about 30 wt %, better still from 0.5 to 20 wt %, relative to the total weight of the composition;

one or more water-soluble dyes, such as the disodium salt of ponceau, the disodium salt of alizarin green, quinoline yellow, the trisodium salt of amaranth, the disodium salt of tartrazine, the monosodium salt of rhodamine, the disodium salt of fuchsine or xanthophyll, preferably at a rate from 0.1 to about 2 wt %, relative to the total weight of the composition;

one or more fillers, in particular matting agents or fillers with a blurring effect, and in particular powders with a soft-focus effect.

Fillers are to be understood as colorless or white particles, mineral or synthetic, lamellar or nonlamellar, for giving body or stiffness to the composition and/or softness, a matte finish and immediate uniformity on application. These fillers can notably modify or even mask wrinkles by a camouflage effect, or a blurring effect.

The matting agents can be selected from matting polymers (in solution, in dispersion or in the form of particles) and inorganic particles that reduce the sheen of the skin and unify the complexion. The matting agent can notably be selected from a starch, talc, cellulose microbeads, vegetable fibers, synthetic fibers, in particular of polyamides (Nylon® powders such as Nylon-12 (Orgasol® marketed by the company Atochem), microspheres of acrylic copolymers notably of polymethyl (meth)acrylate (PMMA particles or the Micropearl® M310 particles sold by the company Seppic), silica powders, silicone resin powders, powders of acrylic polymers, polyethylene powders, elastomeric cross-linked organopolysiloxanes (marketed notably under the names KSG® by the company Shin-Etsu, under the names Trefil®, BY29® or EPSX® by the company Dow Corning or under the names Gransil® by the company Grant Industries), talc/titanium dioxide/alumina/silica composite powders, powders of silicates, and mixtures thereof.

The filler with a "soft focus" effect can give transparency to the complexion and a blurred effect. Preferably, "soft focus" fillers have an average particle size less than or equal to 30 microns, more preferably less than or equal to 15 microns. These "soft focus" fillers can be of any shape and in particular can be spherical or nonspherical. They can be selected from powdered silica and silicates, notably alumina, powders of the polymethyl methacrylate type (PMMA or Micropearl® M310), talc, silica/$TiO_2$ or silica/zinc oxide composites, polyethylene powders, starch powders, polyamide powders, powders of styrene/acrylic copolymers, silicone elastomers, and mixtures thereof.

Preferably these matting agents or fillers with a soft-focus effect are used at a rate from 0.1 to about 10 wt %, relative to the total weight of the composition, preferably at a rate from 0.1 to about 7 wt %.

One or more pigments—white or colored, nacreous or non-nacreous, mineral and/or organic, coated or uncoated, insoluble in the medium, intended to color and/or opacify the composition. They can be of usual size or nanometric. Among the mineral pigments, we may mention titanium dioxide, optionally surface-treated, oxides of iron or of chromium, manganese violet, ultramarine blue, chromium hydroxide and ferric blue. Among the organic pigments, we may mention carbon black, pigments of the D&C type, and lakes based on carmine, barium, strontium, calcium, aluminum. The nacreous pigments or nacres are iridescent particles that reflect light. These nacreous pigments can be selected from white nacreous pigments such as mica coated with titanium, or with bismuth oxychloride, colored nacreous pigments such as titanium mica with iron oxides. The pigments can have undergone a surface treatment. Preferably, these pigments are used at a rate from 0.1 to about 10 wt %, relative to the total weight of the composition, preferably at a rate from 0.1 to about 5 wt %.

one or more lifting agents. "Lifting agent" means a compound that is able to stretch the skin and, as a result of this stretching effect, smooth the skin and reduce wrinkles and lines or even make them disappear immediately. As lifting agents, we may mention polymers of natural origin; mixed silicates; colloidal particles of inorganic fillers; synthetic polymers; and mixtures thereof. We may notably mention: polymers of vegetable or microbial origin, polymers derived from the appendages of the skin, egg proteins and latices of natural origin. These polymers are preferably hydrophilic. As polymers of vegetable origin, we may mention in particular proteins and hydrolyzates of proteins, and more particularly extracts of cereals, of leguminous plants and of oleaginous plants, such as extracts of maize, rye, wheat, buckwheat, sesame, spelt, pea, tapioca, bean, lentil, soybean and lupine. Other lifting agents that can be used according to the invention are the polysaccharides of natural origin, notably starch derived notably from rice, maize, tapioca, potato, cassava, pea; carrageenans, acacia gums (gum arabic), alginates, agars, gellan gums, xanthan gums, cellulosic polymers and pectins, advantageously in aqueous dispersion of gel microparticles, cellulose derivatives, and mixtures thereof. The synthetic polymers are generally in the form of a latex or a pseudolatex and can be of the polycondensate type or can be obtained by radical polymerization. We may notably mention dispersions of polyester/polyurethane and of polyether/polyurethane. Preferably, the lifting agent is a copolymer of PVP/dimethiconylacrylate and of hydrophilic polyurethane (Aquamere® S-2011® from the company Hydromer).

one or more preservative(s);
sequestering agents such as the salts of EDTA;
perfumes;
and mixtures thereof.

Examples of such additives are notably listed in the CTFA Dictionary (International Cosmetic Ingredient Dictionary and Handbook published by The Cosmetic, Toiletry and Fragrance Association, 11th Edition, 2006), which describes, non-exhaustively, a great variety of cosmetic and pharmaceutical ingredients usually employed in the skin care industry, which are suitable for use as additional ingredients in the compositions according to the present invention.

A person skilled in the art is capable of selecting, from all these possible additives, both the composition and the amount of those to be added to the composition, in such a way that the latter retains all of its properties.

Moreover, the composition according to the present invention can optionally contain various active agents, which can be selected from the group consisting of vitamins, antioxidants, hydrating agents, antipollution agents, keratolytic agents, astringents, anti-inflammatory agents, bleaching agents and agents promoting the microcirculation.

Examples of vitamins include vitamins A, B1, B2, B6, C and E and derivatives thereof, pantothenic acid and derivatives thereof and biotin.

Examples of antioxidants include ascorbic acid and derivatives thereof such as ascorbyl palmitate, ascorbyl tetraisopalmitate, ascorbyl glucoside, magnesium ascorbyl phosphate, sodium ascorbyl phosphate and ascorbyl sorbate; tocopherol and derivatives thereof, such as tocopherol acetate, tocopherol sorbate and other esters of tocopherol; BHT and BHA; gallic acid esters, phosphoric acid, citric acid, maleic acid, malonic acid, succinic acid, fumaric acid, cephaline, hexametaphosphate, phytic acid, and plant extracts, for example from roots of *Zingiber officinale* (ginger) such as Blue Malagasy Ginger marketed by the company BIOLANDES, from *Chondrus crispus, Rhodiola, Thermus thermophilus*, maté leaf, oak wood, bark of Rapet Kayu, Sakura leaves and ylang-ylang leaves.

Examples of hydrating agents include polyethylene glycol, propylene glycol, dipropylene glycol, glycerin, butylene glycol, xylitol, sorbitol, maltitol, mucopolysaccharides, such as chondroitin sulfuric acid, hyaluronic acid of high or of low molecular weight or hyaluronic acid potentiated with a silanol derivative such as the active ingredient Epidermosil® marketed by the company Exymol, and mucoitinsulfuric acid; caronic acid; bile salts, a principal component of NMF (natural moisturizer factor) such as a salt of pyrrolidone carboxylic acid and a salt of lactic acid, an amino acid analog such as urea, cysteine and serine; a soluble short-chain collagen, the PPG diglycerins, the homo- and copolymers of 2-methacryloyloxyethylphosphorylcholine such as Lipidure HM and Lipidure PBM from NOF; allantoin; glycerin derivatives such as PEG/PPG/Polybutylene Glycol-8/5/3 Glycerin from NOF sold under the trade name WilbrideS753 or the glyceryl-polymethacrylate from Sederma sold under the trade name Lubragel®MS; trimethylglycine sold under the trade name Aminocoat® by the company Asahi Kasei Chemicals and various plant extracts such as extracts of *Castanea sativa*, hydrolyzed hazelnut proteins, polysaccharides from *Polianthes tuberosa, Argania spinosa* kernel oil and the extracts of nacre containing a conchiolin that are sold notably by the company Maruzen (Japan) under the trade name Pearl Extract®.

Other examples of hydrating agents include compounds that stimulate the expression of matriptase MT/SP1, such as an extract of carob pulp, as well as agents that stimulate expression of FN3K; agents that increase the proliferation or differentiation of keratinocytes such as extracts of *Thermus thermophilus* or of *Camellia Japonica Alba Plena* flower or of shells of *Theobroma cacao* beans, water-soluble maize extracts, peptide extracts of *Voandzeia subterranea* and niacinamide; epidermal lipids and agents that increase the synthesis of epidermal lipids, either directly, or by stimulating certain β-glucosidases that modulate the deglycosylation of lipid precursors such as glucosylceramide to ceramides, such as phospholipids, ceramides, lupine protein hydrolyzates.

Examples of antipollution agents include the extract of Moringa pterygosperma seeds (for example Purisoft® from LSN); Shea butter extract (for example Detoxyl® from Silab), a mixture of ivy extract, phytic acid, sunflower seed extract (for example Osmopur® from Sederma).

Examples of keratolytic agents include the α-hydroxy acids (for example glycolic, lactic, citric, malic, mandelic, or tartaric acids) and the β-hydroxy acids (for example salicylic acid), and esters thereof, such as the C12-13 alkyl lactates, and plant extracts containing these hydroxy acids, such as extracts of *Hibiscus sabdriffa*.

Examples of anti-inflammatory agents include bisabolol, allantoin, tranexamic acid, zinc oxide, sulfur oxide and derivatives thereof, chondroitin sulfate, glycyrrhizinic acid and derivatives thereof such as the glycyrrhizinates.

Examples of astringents include extracts of hamamelis.

Examples of bleaching agents include arbutin and derivatives thereof, ferulic acid (such as Cytovector®: water, glycol, lecithin, ferulic acid, hydroxyethylcellulose, marketed by BASF) and derivatives thereof, kojic acid, resorcinol, lipoic acid and derivatives thereof such as resveratrol diacetate monolipoate as described in patent application WO2006134282, ellagic acid, leukodopachrome and derivatives thereof, vitamin B3, linoleic acid and derivatives thereof, ceramides and their homologs, a peptide as described in patent application WO2009010356, a bioprecursor as described in patent application WO2006134282 or a tranexamate salt such as the hydrochloride salt of cetyl tranexamate, a licorice extract (extract of *Glycyrrhiza glabra*), which is sold notably by the company Maruzen under the trade name Licorice Extract®, a bleaching agent that also has an antioxidant effect, such as the compounds of vitamin C, including the ascorbate salts, the ascorbyl esters of fatty acids or of sorbic acid, and other derivatives of ascorbic acid, for example, ascorbyl phosphates, such as magnesium ascorbyl phosphate and sodium ascorbyl phosphate, or the esters of saccharide of ascorbic acid, which include, for example, ascorbyl-2-glucoside, L-ascorbate of 2-O-alpha-D-glucopyranosyl, or L-ascorbate of 6-O-beta-D-galactopyranosyl. An active agent of this type is sold in particular by the company DKSH under the trade name Ascorbyl Glucoside®.

Examples of agents promoting the microcirculation include an extract of lupine (such as Eclaline® from Silab), of ruscus, of horse chestnut, of ivy, of ginseng or of melilot, caffeine, nicotinate and derivatives thereof, an extract of alga of *Corallina officinalis* such as that marketed by CODIF; and mixtures thereof. These agents that act on the microcirculation of the skin can be used for preventing dulling of the complexion and/or for improving the uniformity and radiance of the complexion.

The composition used according to the invention can further comprise, in addition to the polypeptide according to the invention, at least one active ingredient selected from: agents that stimulate the expression of tensin 1 such as an elemi extract; agents that stimulate the expression of FN3K and/or of FN3K RP such as an extract of *Butea frondosa*; agents that stimulate the expression of CERT or of ARNT2; agents that stimulate the production of growth factors; antiglycation agents or deglycating agents; agents for increasing the synthesis of collagen or preventing its degradation (anti-collagenase agents, notably inhibitors of matrix metalloproteinases), in particular agents for increasing the synthesis of collagen IV and/or of hyaluronan and/or of fibronectin, such as at least one acylated oligopeptide, notably that marketed by the company SEDERMA under the trade name Matrixyl® 3000; agents for increasing the synthesis of elastin or preventing its degradation (anti-elastase agents); agents for increasing the synthesis of glycosaminoglycans or of proteoglycans or preventing their degradation (anti-proteoglycanase agents) such as the active ingredient Epidermosil® (hyaluronic acid associated with methylsilanetriol) marketed by the company Exsymol; agents for stimulating the synthesis of integrins by the fibroblasts; agents for increasing the proliferation of the fibroblasts; agents facilitating percutaneous absorption such as alcohols, fatty alcohols and fatty acids and the ester or ether derivatives thereof, pyrrolidones, 4-alkyl-oxazolidin-2-ones such as 4-decyloxazolidin-2-one; terpenes, essential oils and α-hydroxy acids; and mixtures thereof, without this list being exhaustive.

FIG. 1: Represents in vitro crosslinking binding assay with peptide PEVQKG (SEQ ID NO: 10), having more than 80% homology with peptide PEVQKP (SEQ ID NO: 15) of LCE6A and one glutamine (Gln, Q)-Lysine (Lys, K) domain. Representative images of human skin cryosections observed with a fluorescence microscope after in vitro crosslinking assay performed with peptide PEVQKG (SEQ ID NO: 10) (A, B) or with peptide PEVQKP (SEQ ID NO: 15) (C, D) in the presence of 5 mM CaCl2) (A, C) or in the presence of EDTA (B, D). The strong labelling of the contour of the granular keratinocytes in (A) shows that the peptide PEVQKG (SEQ ID NO: 10) possesses the ability to bind cornified envelopes, similarly to the positive control (C). Absence of labelling when the assays are performed in the presence of EDTA (B, D) shows that the endogenous transglutaminases, which are calcium-dependent, are necessary for the crosslink.

The invention will now be illustrated by the following nonlimiting examples.

EXAMPLES

Example 1: Cloning of the Complementary DNA Coding for LCE6A and Synthesis of the Polypeptide LCE6A by Genetic Engineering The applicant cloned the complementary DNA (cDNA) coding for human LCE6A, and produced, in bacterial recombinant form, the LCE6A protein fused with glutathione S transferase (GST).

Protocol:

1—Cloning the Complementary DNA Coding for Human LCE6A

The applicant obtained cDNAs produced from a fraction enriched in human granular keratinocytes, as described in previously published works (Toulza et al., Large scale identification of human genes implicated in epidermal barrier function, Genome Biology 2007, 8: R107). These cDNAs were used for cloning the cDNA coding for LCE6A by polymerase chain reaction (PCR) using the primers 5'atgtcacagcagaagcagca3' and 5'gtcgccttcacactcttcctc3'. The PCR product, with a size of 240 base pairs, was inserted in the vector pCR®2.1-TOPO® using the cloning kit TOPO TA Cloning® (Invitrogen), according to the manufacturer's instructions. A positive clone was selected and was designated pCR2.1-TOPO-LCE6A. The plasmid pCR2.1-TOPO-LCE6A was digested by the restriction enzyme EcoRI, and the fragment corresponding to the cDNA LCE6A with 258 base pairs was purified and subcloned into the prokaryotic expression vector pGEX6P1 (GE Healthcare) digested by EcoRI. Directed screening of the clones obtained enabled a clone to be selected, designated pGEX6P1-LCE6A.

2—Synthesis of the Polypeptide LCE6A by Genetic Engineering

*E. coli* BL21-CodonPlus®-DE3-RIL bacteria (Stratagene) were transformed by the plasmid pGEX6P1-LCE6A and production of the LCE6A recombinant protein was carried out as follows: the transformed bacteria were cultured overnight with stirring at 2 revolutions per minute (rpm) at 37° C. in 10 ml of LB-ampicillin-chloramphenicol medium (10 g/l NaCl, 10 g/l tryptone, 8 g/l yeast extract, 100 mg/l ampicillin, 50 mg/ml chloramphenicol, pH7). This culture is used next day for seeding 500 ml of LB-ampicillin-chloramphenicol medium and to continue culture for about 2 h, until the culture has an optical density at 600 nm of between 0.6 and 0.8. Production of the recombinant LCE6A protein fused with glutathione-S-transferase (GST) at its N-terminal end (called GST-LCE6A hereinafter) is then induced by continuing culture for 4 h in the presence of 0.1 mM isopropyl thio-β-D-galactoside (IPTG). The bacterial culture is then placed on ice for 10 minutes, and then centrifuged for 10 minutes at 6000 rpm at +4° C. After removing the supernatant, the pellet is stored for at least 12 h at −20° C.

The bacterial lysate is obtained as follows: the bacterial pellet is suspended in 50 ml of solubilization buffer (20 mM Tris, 150 mM NaCl, 1 mM EDTA, with addition of 100 µl of cocktail of bacterial protease inhibitors (P8465, Sigma)), then centrifuged for 10 minutes at 13 000 rpm at +4° C. The supernatant is removed, and the pellet is suspended in 50 ml of solubilization buffer. 5 ml of lysozyme at 100 mg/ml is added and it is incubated for 15 minutes on ice. Then 500 µl of 1M dithiothreitol and 7.75 ml of Sarkosyl 10% are added, it is mixed by inversion and the suspension is sonicated (ultrasonic cell disruptor XL2000, Misonix) 3 times for 20 seconds with return on ice for 5 minutes between each sonication. The lysate is then centrifuged for 30 minutes at 10 000 rpm+4° C. The supernatant is recovered and 20 ml of Triton-X-100 at 10% and 16.75 ml of solubilization buffer are added to it. Lysis is completed with incubation of this solution for 30 minutes with gentle stirring at room temperature, and then the lysate is filtered (pores with diameter of 0.45 µm).

GST-LCE6A is purified from this bacterial lysate by affinity on a "glutathione-sepharose 4 fast flow" column (2.5 ml of matrix) (GE-Healthcare Amersham) according to the manufacturer's instructions. The filtrate is deposited on the column and the fraction not retained is discarded. The column is rinsed with 40 ml of phosphate buffered saline (PBS) (1.47 mM $KH_2PO_4$, 4.3 mM $Na_2HPO_4$, 137 mM NaCl, 2.7 mM KCl, 0.9 mM $CaCl_2$, pH 7.4) and elution is performed by applying 8 ml of glutathione at 10 mM in buffer Tris 50 mM pH8, then 4 ml of PBS. Twelve 1-ml elution fractions are collected at column outlet. An aliquot of 12.5 µl of each of these fractions is separated by electrophoresis in denaturing conditions SDS-PAGE 15% ("SDS-polyacrylamide gel electrophoresis") and transferred onto a nitrocellulose membrane by electrotransfer. This membrane is then used for testing by Western blotting (immunotransfer) for the presence of the recombinant protein in the elution fractions. The primary antibody is a monoclonal antibody recognizing GST (mouse mAb 26H1, Cell Signaling Technology) used at 1/10000th, the secondary antibody coupled to peroxidase (horseradish peroxidase conjugated-goat anti-mouse IgG (H+L), Zymed) is used at 1/10000th and detection is performed with the reagent ECL (Amersham Pharmacia Biotech). The elution fractions containing the bacterial recombinant protein are combined, dialyzed against 1000 volume of PBS using dialysis bags (MWCO 3500) overnight at +4° C. with stirring. The dialysate is then assayed by Bradford's method using the "BioRad protein assay" kit (BioRad).

The yield is on average 3 mg of recombinant protein per 500 ml of bacterial culture.

Example 2: Investigation of the Expression and of the Localization of the LCE6A Protein in Normal Human Epidermis Protocol:

1. Production and Purification of Rabbit Antiserum Specifically Recognizing the LCE6A Protein:

After analyzing the primary sequence of the LCE6A protein, the applicant selected the polypeptide with 15 amino acids CHSSSQRPEVQKPRR, corresponding to residues 42 to 56 of LCE6A, not homologous with the other proteins of the LCE family, designated SEQ ID NO: 6 hereinafter. This polypeptide was produced and used for immunizing two rabbits (4 successive injections at week 1, 4, 7 and 9). The antiserum is collected in the 11th week. These steps were performed by the company Génosphère Biotechnologies. The antipeptide serum was then purified by affinity by the applicant. For this, the polypeptide corresponding to the amino acid sequence SEQ ID NO: 6 was immobilized on agarose beads using the Sulfolink® kit (Pierce). The beads are incubated with 10 ml of antiserum diluted to ½ in loading buffer "Gentle Ag/Ab binding buffer" (Pierce) for 1 h at room temperature with gentle stirring. The beads are sedimented in a column and the liquid not retained is discarded. The column is rinsed with 25 ml of loading buffer with addition of 0.5 M NaCl, and then 5 ml of loading buffer. The antipeptide serum LCE6A is eluted by depositing 9 ml of "Gentle Ag/Ab elution buffer" (Pierce) on the column, and the reactivity of each of the 9 elution fractions is tested by Western blotting on the GST-LCE6A recombinant protein. Incubation is performed with an aliquot of each of the elution fractions diluted to 1/50th, then with a secondary rabbit anti-immunoglobulin antibody coupled to peroxidase diluted to 1/10000th (Zymed). Detection is performed with the ECL kit (Amersham Pharmacia Biotech). The fractions displaying the highest reactivity against the recombinant protein are combined and dialyzed against 1000 volumes of TBS buffer (0.05 M Tris, 0.15 M NaCl, pH 7.6) using dialysis bags (MWCO 3500) overnight at +4° C. with stirring. The dialysate is concentrated approx. 20-fold by ultrafiltration (Vivaspin 15R, 30000 MWCO, Vivascience). The concentrated dialysate, corresponding to the purified antiserum, is titrated on the recombinant protein by Western Blot. It recognizes 100 ng of GST-LCE6A down to a dilution of 1/2000th.

2. Detection of the LCE6A Protein by Immunohistology:

The expression and localization of the LCE6A protein in the normal human epidermis was analyzed by immunohistochemistry and immunofluorescence using LCE6A antipeptide serum. Samples of normal human abdominal skin were fixed in formol for 24 h and embedded in paraffin. Immunodetection is performed on the sections after unmasking the antigen by incubation for 40 minutes in 50 mM glycine-HCl pH 3.5 at 95° C.

In the immunohistochemistry experiments, immunodetection is performed with the "Impress rabbit" kit (Vector Laboratories) according to the manufacturer's instructions, using the LCE6A antipeptide serum diluted to 1/250th.

In the immunofluorescence experiments, double labeling was carried out using the LCE6A antipeptide serum diluted to 1/100th and a mouse monoclonal antibody directed against (pro)filaggrin (AHF3, Simon et al., J Invest Dermatol 1995, 105: 432) diluted to 1/1000th. The secondary antibodies are anti-mouse immunoglobulin immunoglobulins coupled to AlexaFluor488 and anti-rabbit immunoglobulin immunoglobulins coupled to AlexaFluor555 (Invitrogen), used at 1/1000th.

Results:

The labeling obtained by immunohistochemistry or immunofluorescence with the LCE6A antipeptide serum appears late during epidermal differentiation, at the stratum granulosum/stratum corneum transition and in the lower part of the stratum corneum. Comparison of the labeling obtained with the LCE6A antipeptide serum and the anti (pro)filaggrin monoclonal antibody in immunofluorescence showed that the two proteins, LCE6A and filaggrin, are expressed in the granular layer and at the bottom of the stratum corneum of the human epidermis.

Example 3: Investigation of the Expression and Localization of the LCE6A Protein in the Psoriatic Human Epidermis Protocol:

1. Rabbit Antiserum Specifically Recognizing the LCE6A Protein:

The rabbit antiserum specifically recognizing the human LCE6A protein used is the same as that for which the production and purification were described in example 2.

2. Detection of the LCE6A Protein by Immunohistology:

The expression and localization of the LCE6A protein in normal human epidermis was analyzed by indirect immunofluorescence using the LCE6A antipeptide serum. The samples are from normal human abdominal skin or from psoriatic lesions taken from 15 subjects with psoriasis. These skin samples were cryofixed and stored at −80° C. Cryosections were obtained, dried in the open air for about 2 hours, fixed with acetone for 10 minutes, and then stored at −80° C. Immunodetection is performed by immunofluorescence on the sections after unmasking the antigen by incubation for 20 minutes in "target retrieval solution pH9" (Dako) at 95° C. The LCE6A antipeptide serum is used at a dilution of 1/250th. The secondary antibody is an anti-rabbit immunoglobulin immunoglobulin coupled to AlexaFluor555 (Invitrogen), used at 1/1000th.

Results:

Observation of the sections of skin with lesions obtained from the 15 subjects with psoriasis shows a large drop in expression of LCE6A in the granular layer and the bottom of the stratum corneum of the epidermis, compared with normal skin. It therefore appears that this disease, which displays profound disturbance of keratinocyte proliferation and differentiation, as well as a considerable disturbance of the barrier function of the epidermis, shows a greatly reduced amount of LCE6A protein, expressed by the granular keratinocyte and then incorporated in the cornified envelope.

Example 4: Biochemical and Functional Characterization of LCE6A—Transglutaminase Binding Assay The applicant carried out transglutaminase binding assays in vitro using recombinant LCE6A possessing a C-terminal histidine tag (LCE-His).

1. Cloning the LCE6A-his Protein and Purification:

Protocol:

For cloning the cDNA coding for LCE6A-His, the LCE6A cDNA was amplified by PCR starting from the pGEX6P1-LCE6A vector using the primers 5'catatgt-cacagcagaagcagcaa3' and 5'ctcgaggtcgccttcacactc3'. The PCR product, with a size of 248 base pairs, was inserted in the vector pCR®2.1-TOPO® using the TOPO TA Cloning® cloning kit (Invitrogen), according to the manufacturer's instructions. A positive clone was selected and was designated pCR2.1-TOPO-LCE6A-NdeI-XhoI. This plasmid was digested by the restriction enzymes NdeI and XhoI, and the fragment corresponding to the LCE6A cDNA with 248 base pairs was purified and subcloned into the prokaryotic expression vector pET41b (Novagen) digested by NdeI and XhoI. Screening of the clones obtained made it possible to select a clone that was designated pET41b-LCE6A-His.

E. coli BL21-CodonPlus®-DE3-RIL bacteria (Stratagene) were transformed by the pET41b-LCE6A-His plasmid and production of the recombinant protein was carried out as follows: the transformed bacteria were cultured overnight with stirring at 250 rpm at 37° C. in 10 ml of LB-kanamycin-chloramphenicol medium (10 g/l NaCl, g/1 tryptone, 8 g/l yeast extract, 50 mg/l kanamycin, 50 mg/l chloramphenicol, pH7). This culture is used the next day for seeding 500 ml of LB-kanamycin-chloramphenicol medium and culture is continued for about 2 h, until the culture has an optical density at 600 nm of between 0.6 and 0.8. Production of the recombinant LCE6A-His protein is then induced by continuing culture for 4 h in the presence of 0.1 mM isopropyl thio-β-D-galactoside (IPTG). The bacterial culture is then placed on ice for 10 minutes, and then centrifuged for 10 minutes at 6000 rpm at +4° C. After removing the supernatant, the pellet is stored for at least 12 h at −20° C.

The bacterial lysate is obtained as follows: the bacterial pellet is suspended in 100 ml of lysis buffer (50 mM $NaH_2PO_4$, 300 mM NaCl, 10 mM imidazole, pH8, 0.1 mg/ml lysozyme, with addition of 100 µl of cocktail of bacterial protease inhibitors (P8465, Sigma)) and incubated for 1.5 h with gentle stirring at +4° C. The lysate is sonicated (ultrasonic cell disruptor XL2000, Misonix) 6 times for 5 seconds with return on ice for 5 minutes between each sonication, then centrifuged for 30 minutes at 14 000 rpm+ 4° C. The supernatant is recovered and filtered (pores with diameter of 0.45 µm) prior to purification by affinity on a nickel column (1 ml of matrix) "His-Trap High Performance" (Amersham Biosciences). The column is equilibrated with 10 volumes of lysis buffer, then the lysate is loaded. The liquid not retained is discarded and the column is rinsed with 15 volumes of washing buffer (50 mM $NaH_2PO_4$, 300 mM NaCl, 20 mM imidazole, pH8). Elution is performed with 10 volumes of elution buffer (50 mM $NaH_2PO_4$, 300 mM NaCl, 0.5 M imidazole, pH8). The presence of the recombinant protein in the elution fractions is detected by Western Blot. The primary antibody is an antitetra-His monoclonal antibody (mouse monoclonal IgG1 "Tetra-His antibody", Qiagen) used at 1/2000th, the secondary antibody coupled to peroxidase (horseradish peroxidase conjugated-goat anti-mouse IgG (H+L), Zymed) is used at 1/10000th and detection is performed with the reagent ECL (Amersham Pharmacia Biotech). The elution fractions containing the bacterial recombinant protein are combined and dialyzed against 1000 volumes of PBS using dialysis bags (MWCO 3500) overnight at +4° C. with stirring. The dialysate is then assayed by Bradford's method using the "BioRad protein assay" kit (BioRad). The yield is on average 3 mg of recombinant protein per 500 ml of bacterial culture.

2. In-Vitro Transglutaminase 2 Binding Assay (TGM2):
Protocol:

A binding assay of LCE6A by transglutaminase 2 (transglutaminase purified from guinea pig liver, Sigma T5398) was performed in vitro.

In a first experiment, the applicant tested the capacity of TGM2 to form bridges between LCE-His and a molecule bearing an amine bond, monodansyl cadaverine (MDC). For this, TGM2 (10 ng/μL) was incubated in the presence of 0.35 μg of LCE6A-His in solution in a buffer 50 mM Tris, 100 mM DTT, pH 7.4, with addition of 10 mM $CaCl_2$ and 500 μM MDC (Fluka). After incubation for 2 h or 18 h at 37° C., the reaction is stopped by adding EDTA to final 25 mM. The negative control corresponds to the same experiment performed in the absence of $CaCl_2$ and in the presence of 100 mM of ETDA after incubation for 18 h. The reaction product is separated by SDS-PAGE 15%, then visualized by illumination with UV.

In a second experiment, the applicant also tested the capacity of TGM2 to form bridges of LCE6A with itself. For this, TGM2 (10 ng/μL) was incubated in the presence of 0.35 μg of LCE6A-His in a buffer 50 mM Tris, 100 mM DTT, pH 7.4, with addition of 10 mM $CaCl_2$. After incubation for 2 h or 18 h at 37° C., the reaction is stopped by adding EDTA to final 25 mM. The negative control corresponds to the same experiment performed in the absence of $CaCl_2$ and in the presence of 100 mM of ETDA after incubation for 18 h. The reaction product is separated by SDS-PAGE 15% and transferred onto a nitrocellulose membrane. The intermolecular bonds are visualized by Western Blot as described above with an anti-His antibody (mouse monoclonal IgG1 "Tetra-His antibody", Qiagen).

Results:

In the first experiment, starting from 2 h of incubation, several fluorescent bands were detected, migrating to the height of the free MDC (migration front), or of LCE6A-His (about 17 kDa). Other bands with higher molecular weight, of low intensity, migrate to the size of dimers or multimers of LCE6A-His. No fluorescent band, apart from that corresponding to the free MDC, is detected when the same experiment is performed in the presence of 100 mM EDTA and in the absence of calcium.

In the second experiment, the result of the Western Blot shows a band of about 17 kDa corresponding to monomeric LCE6A-His, and several bands of higher molecular weight migrating to a size equivalent to dimers or multimers of LCE6A-His. Only the band corresponding to monomeric LCE6A-His is detected when the experiment is performed in the same conditions but in the absence of calcium and in the presence of 100 mM of EDTA.

Consequently, these experiments are able to confirm that the LCE6A protein is indeed a substrate of transglutaminase 2. LCE6A behaves both as donor and an acceptor of amino acid residues necessary for binding ε-(γ-glutamyl)lysyl to the transglutaminase.

3. In-Vitro Transglutaminase 3 Binding Assay (TGM3):

A binding assay of LCE6A by transglutaminase 3 (human recombinant transglutaminase 3, R&D Systems) was performed in vitro. These assays are carried out according to the same experimental protocol as that described in example 4 paragraph 2 with transglutaminase 2.

In a first experiment, the applicant tested the capacity of TGM3 to form bridges between LCE-His and monodansyl cadaverine (MDC). For this, TGM3 (10 ng/μL) was incubated in the presence of 0.35 μg of LCE6A-His in solution in a buffer 50 mM Tris, 100 mM DTT, pH 7.4, with addition of 10 mM $CaCl_2$ and 500 μM MDC (Fluka). After incubation for 2 h or 18 h at 37° C., the reaction is stopped by adding EDTA to final 25 mM. The negative control corresponds to the same experiment performed in the absence of $CaCl_2$ and in the presence of 100 mM of ETDA after incubation for 18 h. The reaction product is separated by SDS-PAGE 15%, then visualized by illumination with UV.

In a second experiment, the applicant tested the capacity of TGM3 to form bridges of LCE6A with itself. For this, TGM3 (10 ng/μL) was incubated in the presence of 0.35 μg of LCE6A-His in a buffer 50 mM Tris, 100 mM DTT, pH 7.4, with addition of 10 mM $CaCl_2$. After incubation for 2 h or 18 h at 37° C., the reaction is stopped by adding EDTA to final 25 mM. The negative control corresponds to the same experiment performed in the absence of $CaCl_2$ and in the presence of 100 mM of ETDA after incubation for 18 h. The reaction product is separated by SDS-PAGE 15% and transferred onto a nitrocellulose membrane. The intermolecular bonds are visualized by Western Blot as described above with an anti-His antibody (mouse monoclonal IgG1 "Tetra-His antibody", Qiagen).

Results:

In the first experiment, starting from 2 h of incubation, several fluorescent bands were detected, migrating to the height of the free MDC (migration front), or of LCE6A-His (about 17 kDa). Other bands with higher molecular weight, of low intensity, migrate to the size of dimers or multimers of LCE6A-His. No fluorescent band, apart from that corresponding to the free MDC, is detected when the same experiment is performed in the presence of 100 mM EDTA and in the absence of calcium.

In the second experiment, the result of the Western Blot shows a band of about 17 kDa corresponding to monomeric LCE6A-His, and several bands of higher molecular weight migrating to a size equivalent to dimers or multimers of LCE6A-His. Only the band corresponding to monomeric LCE6A-His is detected when the experiment is performed in the same conditions but in the absence of calcium and in the presence of 100 mM of EDTA.

Consequently, these experiments are able to confirm that the LCE6A protein is indeed a substrate of transglutaminase 3. LCE6A behaves both as donor and an acceptor of amino acid residues necessary for binding ε-(γ-glutamyl)lysyl to transglutaminase. The transglutaminases 1, and 5, which catalyze the same reaction as TGM2, are involved in vivo in formation of the stratum corneum and in formation of the isopeptide bonds necessary for the strength and insolubility of the cornified envelope. LCE6A is therefore, in vitro, the substrate of at least one of the transglutaminases involved, in vivo, in formation of the cornified envelope.

Example 5: Characterization of the Peptide Sequence of LCE6A Involved in Binding to Transglutaminase Protocol:

To determine what region of the LCE6A protein is necessary for binding by the transglutaminases, the applicant arranged for the company MilleGen to synthesize various polypeptides, biotinylated at their N-terminal end, with a length of 9 to 13 amino acids, corresponding to different regions of the amino acid sequence of LCE6A.

These polypeptides were used in binding assays in situ. Cryosections of human abdominal skin, saturated by incubation in the presence of bovine albumin at 1% in PBS for 30 minutes at room temperature, were brought into contact with 100 mM Tris (pH 7.4) containing 100 μM of biotinylated polypeptide and 5 mM of CaCl₂. After incubation for 2 h at room temperature, the reaction is stopped by adding EDTA at 25 mM for 5 minutes. The sections are then incubated in PBS containing 1% of SDS to destroy the noncovalent bonds.

The presence of biotinylated polypeptides bound to the cornified envelopes by the transglutaminases that are present and active in the tissue is detected by incubation of the sections with streptavidin-AlexaFluor555 at 5 μg/ml (Invitrogen) and visualization in the confocal microscope.

A positive control is performed in a similar experiment but by incubating the sections with 100 μM of cadaverine coupled to AlexaFluor555 (Invitrogen) instead of the polypeptides. For the negative controls, the cryosections are incubated with each biotinylated polypeptide or with cadaverine coupled to AlexaFluor555 but incubation is carried out in the presence of 100 mM of EDTA and in the absence of calcium.

Results:

The positive control shows marking of the contour of the granular keratinocytes, corresponding to the region of the section where there are active transglutaminases. The polypeptides corresponding to the amino acid sequences SEQ ID NO: 3, 4 and 5 show similar marking to that obtained after incubation with cadaverine-AlexaFluor555, whereas no marking is obtained when these same polypeptides or cadaverine-AlexaFluor555 are incubated in the presence of EDTA and in the absence of calcium. Incubation of the sections in the presence of calcium with the polypeptide RPAPPPIS-GGGYRAR (SEQ ID NO: 19), whose sequence does not correspond to any fragment of LCE6A, does not give any pericellular marking of the keratinocytes of the granular layer. Finally, the polypeptide MSQAKQQSW (SEQ ID NO: 17) corresponding to the mutated SEQ ID NO: 3, and the polypeptide EVAKPRRARQALR (SEQ ID NO: 18) corresponding to the mutated SEQ ID NO: 5, does not give any pericellular marking of the keratinocytes of the granular layer.

Consequently, the amino acid sequences SEQ ID NO: 3, 4 and 5 contain the residues necessary for the transglutaminases present in the granular layer of the human epidermis for establishing covalent bonds with the cornified envelope. The loss of capacity for binding the cornified envelopes of the polypeptides corresponding to the mutated SEQ ID NO: 1 and No. 3 suggests that linking of a glutamine residue (Q) and a lysine residue (K) in the sequence of the LCE6A protein is necessary to permit said binding.

Example 6: Cosmetic Composition (O/W Serum)

The following composition can be prepared conventionally by a person skilled in the art. The quantities stated below are expressed in percentages by weight. The ingredients shown in capital letters are identified according to the INCI names.

| INCI Name | % (w/w) |
|---|---|
| Water | Q.S. 100.00 |
| Chelating agent | 0.05 |
| pH adjuster | 0.05 |
| Preservative | 0.05 |
| Glycol | 3.25 |
| AMMONIUM ACRYLOYLDIMETHYLTAURATE/ VP COPOLYMER | 1.20 |
| ACRYLATES/C10-30 ALKYL ACRYLATE CROSSPOLYMER | 0.20 |
| GLYCERIN | 3.00 |
| GLYCERYLPOLYMETHACRYLATE | 4.18 |
| SODIUM ACETYLATED HYALURONATE | 0.05 |
| Oil | 10.00 |
| ALCOHOL | 8.00 |
| PERFUMES | 0.30 |
| Polypeptide SEQ ID NO: 4 obtained according to example 4 | 0.05 |

This composition can be applied daily, in the morning and/or in the evening, on skin that is particularly dehydrated and/or exposed to aggressive environmental factors, to improve comfort and make the complexion uniform.

Example 7: In Vitro Crosslinking Binding Assay with Short Peptides Analogues of LCE6A (SEQ ID NO: 2) Fragments Aim: To determine if short peptides derived from SEQ ID NO: 2, having at least one glutamine (Gln, Q)-Lysine (Lys, K) domain and having at least 80% homology with fragments of SEQ ID NO:2, still possess the ability to be crosslinked to cornified envelopes by endogenous transglutaminase.

Protocol: The following short peptides derived from the amino acid sequences PEVQKP of LCE6A (amino-acids 49 to 54 of SEQ ID NO:2), which sequences meet the criteria defined above and are biotinylated at their amino-terminus, were synthesized: PGVQKP (SEQ ID NO: 7), PEGQKP (SEQ ID NO: 8), GEVQKP (SEQ ID No: 9), PEVQKG (SEQ ID No: 10).

These peptides were used at a concentration of 100 μM in in situ binding assays. Cryosections of human abdominal skin, saturated by incubation in the presence of bovine albumin at 1% in PBS for 30 minutes at room temperature, were brought into contact with 100 mM Tris (pH 7.4) containing 100 μM of biotinylated polypeptide and 5 mM of CaCl2). After incubation for 2 h at room temperature, the reaction was stopped by adding EDTA at 25 mM for 20 minutes. The sections were then incubated in PBS containing 1% of SDS to destroy the noncovalent bonds. The presence of biotinylated polypeptides bound to the cornified envelopes by the transglutaminases that are present and active in the tissue was detected by incubation of the sections with streptavidin-AlexaFluor555 at 5 μg/ml (Invitrogen) and visualization in the fluorescence microscope. A positive control was performed in a similar experiment but by incubating the sections with 100 μM of the peptide PEVQKP of LCE6A (amino-acids 49 to 54 of SEQ ID NO: 2). For the negative control, the cryosections were incubated with each biotinylated polypeptide but incubation was carried out in the presence of 100 mM of EDTA and in the absence of calcium.

Results: The positive control shows labelling of the contour of the granular keratinocytes, corresponding to the region of the section where there are active transglutaminases. The tested peptides show similar labelling (see e.g. FIG. 1 for peptide PEVQKG (SEQ ID No: 10) to that obtained after incubation with the positive control, whereas no labelling is obtained when these same peptides are incubated in the presence of EDTA and in the absence of calcium. Consequently, the tested peptides derived from SEQ ID NO:2, having at least one glutamine (Gln, Q)-Lysine (Lys, K) domain and having at least 80% homology with said fragment of SEQ ID NO: 2, still possess the ability to bind cornified envelopes.

The invention claimed is:

1. A cosmetic method for reinforcing the barrier function of the skin, comprising a step of administering to the skin of a subject, at least one analog of a fragment of at least 5 consecutive amino acids of the sequence SEQ ID No:2 in an amount sufficient for reinforcing the barrier function of the skin by establishing covalent bonds between peptides belonging to the family of late cornified envelope proteins (LCE) and the cornified envelopes in the stratum corneum of the epidermis under the action of endogenous transglutaminases; said analog consisting of a peptide of 5 to 15 amino acids having at least one glutamine (Gln)-lysine (Lys) domain and wherein the analog consisting of 5 to 15 amino acids as a whole has at least 80% of sequence identity with one of said fragments of the sequence SEQ ID NO:2, wherein said analog has an amino acid sequence selected from the group consisting of PGVQKP (SEQ ID NO: 7), PEGQKP (SEQ ID NO: 8), GEVQKP (SEQ ID NO: 9), PEVQKG (SEQ ID NO: 10), QKQTS (SEQ ID NO: 11), STQKQ (SEQ ID NO: 12), SQQKT (SEQ ID NO: 13) and QKTQS (SEQ ID NO: 14).

2. A therapeutic method for reinforcing the barrier function of the skin, comprising a step of administering to a subject in need thereof at least one analog of a fragment of at least 5 consecutive amino acids of the sequence SEQ ID No:2 in an amount sufficient for reinforcing the barrier function of the skin by establishing covalent bonds between peptides belonging to the family of late cornified envelope proteins (LCE) and the cornified envelopes in the stratum corneum of the epidermis under the action of endogenous transglutaminases; said analog being a peptide of 5 to 15 amino acids having at least one glutamine (Gln)-lysine (Lys) domain and at least 80% of sequence identity with one of said fragments of the sequence SEQ ID NO:2, wherein said analog has an amino acid sequence selected from the group consisting of PGVQKP (SEQ ID NO: 7), PEGQKP (SEQ ID NO: 8), GEVQKP (SEQ ID NO: 9), PEVQKG (SEQ ID NO: 10), QKQTS (SEQ ID NO: 11), STQKQ (SEQ ID NO: 12), SQQKT (SEQ ID NO: 13) and QKTQS (SEQ ID NO: 14).

* * * * *

SEQUENCE LISTING

<160> NUMBER OF SEQ ID NOS: 19

<210> SEQ ID NO 1
<211> LENGTH: 641
<212> TYPE: DNA
<213> ORGANISM: Homo sapiens

<400> SEQUENCE: 1

```
acacaaggcc tccagactcc tcctgggata acttgtccac acatcttcca ctagggtaag      60
gctacttctg gctgaggaga cacttggatg tagctcaagt gctgcttagg cagtcctgat     120
ctctcctctc gtctcttccc agggagctga aaagccagat tcgacctggt agccaagcaa     180
tgtcacagca gaagcagcaa tcttggaagc ctccaaatgt tcccaaatgc tcccctcccc     240
aaagatcaaa cccctgccta gctccctact cgactccttg tggtgctccc cattcagaag     300
gttgtcattc cagttcccaa aggcctgagg ttcagaagcc taggagggct cgtcaaaagc     360
tgcgctgcct aagtaggggc acaacctacc actgcaaaga ggaagagtgt gaaggcgact     420
gagcccagaa gagttgaggc acaggtgcag ttactctctc cctgccccac ctttgggtac     480
taattccccc ttggaaagcc aggccctcaa cctctcattt ggactgagaa acacttcctg     540
atccccagct ctagagaagc gagaactagg ctgagccacg ctgctactgc tctcttccat     600
tcaccccttc agctcagcaa caataaagct gctttacttg g                         641
```

<210> SEQ ID NO 2
<211> LENGTH: 80
<212> TYPE: PRT
<213> ORGANISM: Homo sapiens

<400> SEQUENCE: 2

```
Met Ser Gln Gln Lys Gln Gln Ser Trp Lys Pro Pro Asn Val Pro Lys
1               5                   10                  15

Cys Ser Pro Pro Gln Arg Ser Asn Pro Cys Leu Ala Pro Tyr Ser Thr
            20                  25                  30

Pro Cys Gly Ala Pro His Ser Glu Gly Cys His Ser Ser Ser Gln Arg
        35                  40                  45

Pro Glu Val Gln Lys Pro Arg Arg Ala Arg Gln Lys Leu Arg Cys Leu
    50                  55                  60

Ser Arg Gly Thr Thr Tyr His Cys Lys Glu Glu Glu Cys Glu Gly Asp
65                  70                  75                  80
```

<210> SEQ ID NO 3
<211> LENGTH: 9
<212> TYPE: PRT
<213> ORGANISM: Artificial
<220> FEATURE:
<223> OTHER INFORMATION: Designed peptide based on homology to amino
      acid residue 1 to 9 from Protein LCE6A

<400> SEQUENCE: 3

```
Met Ser Gln Gln Lys Gln Gln Ser Trp
1               5
```

<210> SEQ ID NO 4
<211> LENGTH: 11
<212> TYPE: PRT
<213> ORGANISM: Artificial
<220> FEATURE:
<223> OTHER INFORMATION: Designed peptide based on homology to amino
      acid residue 45 to 55 from Protein LCE6A

<400> SEQUENCE: 4

```
Ser Ser Gln Arg Pro Glu Val Gln Lys Pro Arg
1               5                   10
```

<210> SEQ ID NO 5
<211> LENGTH: 13
<212> TYPE: PRT
<213> ORGANISM: Artificial
<220> FEATURE:
<223> OTHER INFORMATION: Designed peptide based on homology to amino
      acid residue 50 to 62 from Protein LCE6A

<400> SEQUENCE: 5

```
Glu Val Gln Lys Pro Arg Arg Ala Arg Gln Lys Leu Arg
1               5                   10
```

<210> SEQ ID NO 6
<211> LENGTH: 15
<212> TYPE: PRT
<213> ORGANISM: Artificial
<220> FEATURE:
<223> OTHER INFORMATION: Designed peptide based on homology to amino
      acid residue 42 to 56 from Protein LCE6A

<400> SEQUENCE: 6

```
Cys His Ser Ser Ser Gln Arg Pro Glu Val Gln Lys Pro Arg Arg
1               5                   10                  15
```

<210> SEQ ID NO 7
<211> LENGTH: 6
<212> TYPE: PRT
<213> ORGANISM: Artificial Sequence
<220> FEATURE:
<223> OTHER INFORMATION: Designed peptide based on homology to amino
      acid residue 49 to 54 from Protein LCE6A

<400> SEQUENCE: 7

```
Pro Gly Val Gln Lys Pro
1               5
```

<210> SEQ ID NO 8
<211> LENGTH: 6
<212> TYPE: PRT
<213> ORGANISM: Artificial Sequence
<220> FEATURE:
<223> OTHER INFORMATION: Designed peptide based on homology to amino
      acid residue 49 to 54 from Protein LCE6A

<400> SEQUENCE: 8

```
Pro Glu Gly Gln Lys Pro
1               5
```

<210> SEQ ID NO 9
<211> LENGTH: 6
<212> TYPE: PRT
<213> ORGANISM: Artificial Sequence
<220> FEATURE:

<223> OTHER INFORMATION: Designed peptide based on homology to amino
      acid residue 49 to 54 from Protein LCE6A

<400> SEQUENCE: 9

Gly Glu Val Gln Lys Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Designed peptide based on homology to amino
      acid residue 49 to 54 from Protein LCE6A

<400> SEQUENCE: 10

Pro Glu Val Gln Lys Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Designed peptide based on homology to amino
      acid residue 4 to 8 from Protein LCE6A

<400> SEQUENCE: 11

Gln Lys Gln Thr Ser
1               5

<210> SEQ ID NO 12
<211> LENGTH: 5
<212> TYPE: PRT
<213> ORGANISM: Artificial Sequence
<220> FEATURE:
<223> OTHER INFORMATION: analog

<400> SEQUENCE: 12

Ser Thr Gln Lys Gln
1               5

<210> SEQ ID NO 13
<211> LENGTH: 5
<212> TYPE: PRT
<213> ORGANISM: Artificial Sequence
<220> FEATURE:
<223> OTHER INFORMATION: Analog

<400> SEQUENCE: 13

Ser Gln Gln Lys Thr
1               5

<210> SEQ ID NO 14
<211> LENGTH: 5
<212> TYPE: PRT
<213> ORGANISM: Artificial Sequence
<220> FEATURE:
<223> OTHER INFORMATION: analog

<400> SEQUENCE: 14

Gln Lys Thr Gln Ser
1               5

<210> SEQ ID NO 15
<211> LENGTH: 6
<212> TYPE: PRT

```
<213> ORGANISM: Artificial Sequence
<220> FEATURE:
<223> OTHER INFORMATION: fragment

<400> SEQUENCE: 15

Pro Glu Val Gln Lys Pro
1               5

<210> SEQ ID NO 16
<211> LENGTH: 7
<212> TYPE: PRT
<213> ORGANISM: Artificial Sequence
<220> FEATURE:
<223> OTHER INFORMATION: fragment

<400> SEQUENCE: 16

Ser Gln Gln Lys Gln Gln Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Mutated peptide of SEQ ID NO: 3

<400> SEQUENCE: 17

Met Ser Gln Ala Lys Gln Gln Ser Trp
1               5

<210> SEQ ID NO 18
<211> LENGTH: 13
<212> TYPE: PRT
<213> ORGANISM: Artificial Sequence
<220> FEATURE:
<223> OTHER INFORMATION: Mutated peptide of SEQ ID NO: 5

<400> SEQUENCE: 18

Glu Val Ala Lys Pro Arg Arg Ala Arg Gln Ala Leu Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Control peptide of SEQ ID NO: 19

<400> SEQUENCE: 19

Arg Pro Ala Pro Pro Pro Ile Ser Gly Gly Gly Tyr Arg Ala Arg
1               5                   10                  15
```